US008642651B2

(12) United States Patent  (10) Patent No.: US 8,642,651 B2
Miljkovic et al.  (45) Date of Patent: Feb. 4, 2014

(54) METHODS AND COMPOSITIONS FOR IMPROVED CHROMIUM COMPLEXES

(75) Inventors: Dusan Miljkovic, San Diego, CA (US); Jovan Hranisavljevic, Belgrade (RS); Zbigniew Pietrzkowski, San Diego, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 201 days.

(21) Appl. No.: 13/175,354

(22) Filed: Jul. 1, 2011

(65) Prior Publication Data
US 2011/0263702 A1 Oct. 27, 2011

Related U.S. Application Data

(60) Division of application No. 11/035,109, filed on Jan. 12, 2005, now abandoned, which is a continuation-in-part of application No. PCT/US2004/025026, filed on Aug. 3, 2004.

(51) Int. Cl.
A61K 39/385 (2006.01)
A61K 31/28 (2006.01)
A01N 43/00 (2006.01)

(52) U.S. Cl.
USPC ............. 514/492; 514/183; 424/193.1

(58) Field of Classification Search
None
See application file for complete search history.

(56) References Cited

U.S. PATENT DOCUMENTS

| | | |
|---|---|---|
| 3,732,627 A | 5/1973 | Wertheim |
| 3,914,410 A | 10/1975 | Godfrey |
| 3,925,433 A | 12/1975 | Abdel-Monem et al. |
| 4,343,905 A | 8/1982 | Szalay |
| 4,348,483 A | 9/1982 | Skogerson |
| 4,571,391 A | 2/1986 | Riley et al. |
| 5,266,560 A | 11/1993 | Furman et al. |
| 5,846,581 A | 12/1998 | Catron |
| 5,872,102 A | 2/1999 | Vincent et al. |
| 6,071,545 A | 6/2000 | Hendler et al. |
| 6,140,107 A | 10/2000 | Yang et al. |
| 6,149,948 A | 11/2000 | Vincent |
| 6,248,323 B1 | 6/2001 | Arnold et al. |
| 6,261,606 B1 | 7/2001 | Mirsky et al. |
| 6,303,158 B1 | 10/2001 | Odgaard et al. |
| 6,323,192 B1 | 11/2001 | Harpe et al. |
| 6,352,714 B1 | 3/2002 | Erickson et al. |
| 6,379,693 B1 | 4/2002 | Mao et al. |
| 6,548,687 B1 | 4/2003 | Yu et al. |
| 6,558,666 B1 | 5/2003 | Anderson |
| 6,689,383 B1 | 2/2004 | Anderson et al. |
| 6,713,469 B2 | 3/2004 | de la Harpe et al. |
| 6,733,793 B2 | 5/2004 | Pacioretty et al. |
| 6,809,115 B2 | 10/2004 | Katz et al. |
| 2001/0022979 A1 | 9/2001 | Mirsky et al. |
| 2002/0169204 A1 | 11/2002 | Vincent et al. |
| 2002/0197340 A1 | 12/2002 | de la Harpe et al. |
| 2003/0133992 A1 | 7/2003 | Bagchi et al. |
| 2003/0224061 A1 | 12/2003 | Pacioretty et al. |
| 2003/0228394 A1 | 12/2003 | Abdel-Monem et al. |
| 2004/0005368 A1 | 1/2004 | Mann et al. |
| 2004/0106591 A1 | 6/2004 | Pacioretty et al. |

FOREIGN PATENT DOCUMENTS

| | | |
|---|---|---|
| EP | 0037144 | 10/1981 |
| EP | 0248057 | 5/1992 |
| WO | 02/056889 | 7/2002 |
| WO | 03/101436 | 12/2003 |
| WO | 2004/022083 | 3/2004 |

OTHER PUBLICATIONS

Davis, et al., "A biologically active form of chromium may activate a membrane phosphotyrosine phosphatase (PTP)", Biochemistry, Oct. 1, 1996, vol. 35, No. 39, pp. 12963-12969.

Yamamoto et al., "Isolation of a biologically active low-molecular-mass chromium compound from rabbit liver", European Journal of Biochemistry, 1987 Jin 15, vol. 165, No. 3, pp, 627-631.

Zetic, "Chromium uptake by *Saccaromyces* cereviswww and isolation of glucose tolerance factor from yeast biomass", Journal of Biosciences, Indian Academy of Sciences, Jun. 2001, vol. 26, No. 2, pp. 217-223.

Houseknecht, K.L. et al., "Dietary Conjugated Linoleic Acid Normalizes Impaired Glucose Tolerance in the Zucker Diabetic Fatty falfa Rat", Biochemical and Biophysical Research Communications, Feb. 5, 1998, vol. 224, No. 3, pp. 678-682.

Demirci, A. et al., "Enhanced Organically Bound Chromium Yeast Production", Journal of Agricultural Food Chemistry, 2000, vol. 48, No. 2, pp. 531-536.

Anderson, R.A. et al., "Factors Affecting the Retention and Extraction of Yeast Chromium", Journal of Agricultural Food Chemistry, 1978, vol. 26, No. 4, pp. 858-861.

*Primary Examiner* — Kyle Purdy
(74) *Attorney, Agent, or Firm* — Fish & Associates, PC

(57) ABSTRACT

Complex metal-containing matrices, and especially chromium-containing matrices are produced from a water soluble preparation that is derived from an item suitable for animal (and most typically human) consumption. In particularly contemplated aspects, the water soluble preparation is an extract or filtrate of disintegrated brewer's yeast, and the so prepared complex mixture is combined with a chromium-$3^+$ ions.

10 Claims, 1 Drawing Sheet

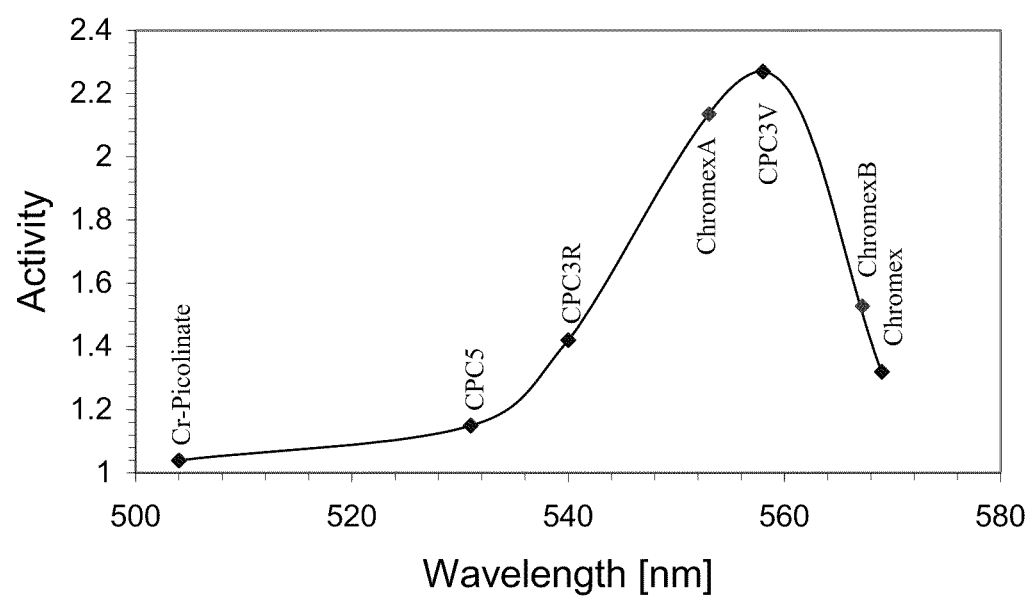

METHODS AND COMPOSITIONS FOR IMPROVED CHROMIUM COMPLEXES

This application is a divisional application of U.S. application Ser. No. 11/035,109 filed Jan. 12, 2005 now abandoned which is a continuation-in-part application of International Patent Application with the serial number PCT/US04/25026, which designates the U.S., filed Aug. 3, 2004.

FIELD OF THE INVENTION

The field of the invention is chromium-containing nutritional compositions and methods, and particularly those with enhanced biological activity and/or absorption.

BACKGROUND OF THE INVENTION

Numerous chromium-containing compositions are well known in the art, however, all or almost all of them suffer from one or more disadvantages. Most significantly, while some of the chromium-containing supplements are embroiled in toxicity issues (e.g., Cr-picolinate), others have only relatively low solubility and/or bioavailability (e.g., chromium yeast), or are expensive (e.g., chromium lactoferrin) in their production.

For example, WO 03/101436 and U.S. Pat. No. 3,925,433 describe various alpha amino acid complexes with $Cr^{3+}$ in nutritional supplements. Similarly, pure alpha amino acid chromium complexes are taught in US 2003/0228394 as animal feed additive. To increase bioavailability of chromium from amino acid complexes, histidine or threonine may be employed as main ligand as reported in U.S. Pat. Nos. 6,689,383, and 6,548,687, respectively. Where desirable, non-proteinogenic amino acid complexes with chromium may be prepared as disclosed in U.S. Pat. No. 6,071,545 and US 2004/0106591. Amino acid containing mixed complexes are taught in WO 02/056889, where an amino acid and nicotinic acid act as ligands. While amino acid ligands are typically considered nutritionally safe, amino acid complexes formed with chromium tend to pose several drawbacks. Among other things, bioavailability of the chromium from the complex is often relatively low. Furthermore, at least some of such complexes have displayed toxicity to some degree.

To overcome at least some of the problems associated with amino acid complexes, non-amino acid ligands (e.g., nicotinate and picolinic acid) are relatively common and often exhibit improved bioavailability, and may further be employed in mixed complexes and/or combination formulations. For example, known non-amino acid chromium complexes include polynicotinate chromium complexes as described in U.S. Pat. No. 6,323,192. Similarly, complexes in which niacin binds chromium were reported as reducing blood glucose in US 2003/0133992. In yet another example, chromium arginate or chromium chalidamate were used as defined and water soluble chromium complexes that were administered in combination with an oxygen uptake enhancer as described in US 2004/00053688. Still further known preparations include those in which Cr-picolinate or Cr-polynicotinate are combined with a cyclooxygenase inhibitor as described in U.S. Pat. No. 6,713,469, or with conjugated linoleic acid or conjugated linoleic alcohol as taught in U.S. Pat. No. 6,809,115.

Other isolated and defined chromium ligands include sucrose as taught in U.S. Pat. No. 3,914,410, acetylacetonate as taught in U.S. Pat. No. 4,571,391, short chain carboxylic acids as described in U.S. Pat. No. 5,846,581 and U.S. Pat. No. 6,303,158, or selected synthetic peptide-like ligands as described in U.S. Pat. No. 5,266,560. Similarly, chromium carnitine complexes in combination with vanadyl sulfate, lipoic acid and other ingredients were reported in U.S. Pat. No. 6,733,793, while EP 0 037 144 describes a negatively charged C3-type ligand (e.g., optionally substituted malonaldehyde complexes). In U.S. Pat. No. 6,149,948, a complex of the formula $[Cr_3O(O_2CCH_2CH_3)_6(H_2O)_3]^+$ is used as a chromium carrier. While such defined complexes tend to overcome at least some of the difficulties associated with amino acid ligands, toxicity issues frequently remain, particularly at relatively high dosages, and/or where the compounds are administered over a relatively long period.

Toxicity may be reduced to at least some degree where specific naturally occurring ligands are selected. For example, isolated bovine chromium-binding protein (e.g., Biochemistry. 1996 Oct. 1; 35(39):12963-9, or Eur J. Biochem. 1987 Jun. 15; 165(3):627-31) was described as a source of chromium supplementation as taught in U.S. Pat. No. 5,872,102. Similarly, lactoferrin was reported as a chromium ligand in U.S. Pat. No. 6,379,693, and in yet another example (see e.g., WO 04/022083), proteolysis-derived low-molecular weight peptides are employed as ligands, that preferably have a proline terminus. Alternatively, oxidized leather scrap hydrolysate from leather tanning refuse was reported as a carrier for chromium in the preparation of animal feed as reported in U.S. Pat. No. 6,352,714. While many hydrolyzed protein preparations are often low- or even non-toxic, various difficulties nevertheless remain. Among other problems, crude hydrolysate generally has an off-taste that is hard to mask, and where the hydrolysate is purified or otherwise processed, production costs often significantly increase. Still further, the use of hydrolytic enzymes may pose a health concern where the enzymes are not properly inactivated.

In yet another known approach of preparing chromium-containing supplements, yeast is cultivated in a medium that includes a chromium source, which provides the chromium to the yeast cell that is subsequently harvested, pasteurized, and optionally dried and/or pulverized. Such products are typically known as chromium yeast products. For example, a common preparation of a chromium yeast product is described in U.S. Pat. Nos. 4,348,483 and 4,343,905 in which the yeast is incubated with a non-toxic chromium compound to form a chromium-enriched yeast cell preparation. The so fermented yeast is then isolated and/or powderized to provide the chromium supplement. To improve the chromium content, selected yeast strains for cultivation of yeast in a metal-containing medium are described in U.S. Pat. No. 6,140,107. Alternatively, or additionally, mixed amino acid nicotinate chromium complexes can be used in the fermentation medium to boost the chromium content of a yeast as described in U.S. Pat. No. 6,248,323. While such preparations are often well tolerated, the low solubility of the chromium yeast product frequently poses a significant hurdle to incorporate such products into a food or beverage. Moreover, and at least in part due to the relatively poor solubility, bioavailability of chromium from such yeast products is typically low.

Yeast has also been used as starting material to purify defined and metabolically active substances as described in U.S. Pat. No. 6,261,606. Similarly, EP 0 248 057 describes isolation of a glucose tolerance factor from yeast. Surprisingly, such isolated factor was free of chromium and was identified as a quinoline compound. However, isolation of such substances is typically labor intensive and therefore often not economic.

Thus, while there are numerous chromium complexes known in the art, toxicity, low bioavailability, and/or low water solubility limit the usefulness of these complexes.

Therefore, there is a constant need to find new chromium compounds/complexes that have higher biological activity/bioavailability, higher safety/less toxicity, sufficient chemical stability and high water solubility.

SUMMARY OF THE INVENTION

The present invention is directed to compositions and methods for water soluble, highly bioavailable chromium-containing complex matrices. Preferably, contemplated matrices are prepared from a filtered or otherwise clarified solution of a disintegrate of an edible (and most typically cellular) material, wherein the clarified solution is combined with a metal (preferably $Cr^{3+}$) to form a complex between the metal and one or more components in the matrix.

Contemplated complex matrices are most preferably formulated for human consumption. For example, the complex matrices may be incorporated into a food item (e.g., snack bar, cereal, etc.), a beverage (e.g., sports drink, liquid diet formulation, etc.), or formulated as a pill or other orally administered dosage form, optionally in combination with other nutritionally relevant compounds (e.g., metabolic modulators, conjugated linoleic acid, etc.).

Therefore, in one aspect of the inventive subject matter, the inventors contemplate a metal-containing substantially completely water soluble complex matrix that is formulated for mammalian consumption. Preferably, the matrix comprises a water soluble fraction of a cellular lysate (most preferably brewer's yeast lysate). The cellular lysate may further be dehydrated (e.g., freeze-dried or spray dried) before or after combination with the meta, which is most preferably chromium-$3^+$. It is still further contemplated that such complex matrices are prepared under conditions that will provide a matrix with an absorption maximum at a wavelength between 550 nm and 570 nm.

In another aspect of the inventive subject matter, a method of preparing a chromium-containing product includes a step in which a water soluble complex preparation is prepared from an edible material. In another step, the preparation is combined with a trivalent chromium ion under conditions effective to form a complex between a component of the preparation and the chromium ion. Most preferably, the conditions are selected such that the complex between the component of the preparation and the chromium ion has an absorption maximum at a wavelength between 545 nm and 565 nm. It is further preferred that the step of preparing includes a step of disintegrating a cellular edible material, and an optional step of removing (e.g., via filtration or centrifugation) at least part of undissolved materials from the disintegrated material.

The chromium is preferably added to the disintegrated material while the material is in a liquid form. However, alternative addition protocols are also contemplated. In yet further preferred examples, the so formed chromium-containing product may be used in a liquid form or in an at least partially dehydrated form (e.g., freeze-dried, or gelled). Especially contemplated edible materials include cellular materials from plants (e.g., fruits or portion of fruits, leaves, seeds, vegetables, etc.), fungi (e.g., brewer's yeast), and animals (e.g., beef, poultry, etc.).

Consequently, in a still further aspect of the inventive subject matter, a food item includes a chromium-containing complex having an absorption maximum at a wavelength between 545 nm and 565 nm, wherein the complex is present in an amount effective to reduce fasting blood glucose in a mammal ingesting the food item. Most preferably, the complex in such food items is substantially completely water soluble, and/or comprises a water soluble extract from a cellular edible item (e.g., brewer's yeast).

Various objects, features, aspects and advantages of the present invention will become more apparent from the following detailed description of preferred embodiments of the invention.

BRIEF DESCRIPTION OF THE DRAWING

FIG. 1 is an exemplary graph depicting the correlation between biological activity and spectral characteristics (here: absorption between 500 nm and 600 nm) of selected chromium-containing compositions.

DETAILED DESCRIPTION

The inventors have unexpectedly discovered that water soluble metal complexes can be prepared from an edible complex matrix, wherein the metal has a high bioavailability. Moreover, with particular relevance to chromium, the inventors discovered that the bioavailability and/or biological effect of chromium appears to be a function of the spectral characteristics.

As used herein, the term "metal-fortified" in conjunction with a composition means that the composition has a metal content that is intentionally raised above a natural metal content of that composition. As also used herein, the term "substantially completely water soluble" refers to a solubility of at least 90 wt %, more typically of at least 95 wt %, and most typically of at least 98 wt %. As further used herein, the term "complex matrix" refers to a composition of matter that comprises at least one hundred, more typically at least 1000, and most typically at least 5000 chemically distinct components, which may or may not be known in at least one of their identity and quantity. As still further used herein, the term "mammalian consumption" refers to oral administration to a mammal, and most typically in solid and/or liquid form to a human.

In one preferred exemplary aspect of the inventive subject matter, a chromium-fortified and substantially completely water soluble complex matrix is prepared by a reaction of water soluble brewer's yeast extract and chromium chloride hexahydrate. Most typically, baker's or brewer's yeast is grown to a desired density, optionally washed and harvested. The cells are then suspended in an aqueous solution and disintegrated (e.g., via French press, ultrasound, shear-homogenizer, etc.). Preferably, the so prepared lysate is cleared to produce an aqueous yeast extract. Typically, clearing is done using centrifugation or filtration.

It should be recognized that the extract may further be processed to achieve one or more desired properties. For example, nucleic acids may be removed to reduce the purine content, or protein may be removed or added to achieve an especially desirable nutritional profile. In other contemplated examples, the aqueous extract may be chemically and/or physically fractionated (e.g., via solvent extraction or size exclusion chromatography) to enrich the matrix in one or more beneficial or otherwise desirable components. After the matrix material is prepared, chromium is typically added in the form of a trivalent chromium ion or salt in a predetermined quantity (e.g., to a final concentration of between about 0.1 mcg/ml to 10 mg/ml). It should be particularly recognized that the chromium ions will form numerous chemically distinct complexes with one or more components in the matrix (e.g., with a peptide, a polysaccharide, a lipoprotein, a nucleic acid, etc.), and that such complexes are sufficiently stable and water soluble. In most typical examples, such prepared compositions are substantially completely water soluble.

Thus, one significant consequence of using aqueous matrices is that the chromium is complexed or otherwise bound to the complex matrix by a material that is a priori water soluble. Based on the assumed molar excess of potential binding/complexing sites for the chromium ions, complexation of the chromium ions will not (or only to a negligible extent) alter the water solubility of the complex matrix. Such approach is clearly superior to conventionally produced chromium yeast as a substantial portion of chromium yeast in insoluble, and with that not available for release of the chromium. For example, where chromium is bound to a membrane or lipopolysaccharide, chromium is not available for hydrophilic exchange.

It is generally contemplated that the chromium fortified and substantially completely water soluble complex matrices will then be formulated for mammalian consumption, which may be in numerous forms. For example, the fortified matrices may be prepared in dehydrated form (e.g., spray-dried, freeze-dried, triple point dried, etc.) as a powder, pill, or otherwise dried form. Alternatively, aqueous or gel forms are also deemed suitable, especially when such forms are combined with a fluid or gel-like nutrient (e.g., sports drink, syrup, preserve, etc.). It should further be appreciated that contemplated fortified matrices may also be combined with any other nutrient for human (or other mammalian) consumption, and all known nutrients are deemed suitable for combination with fortified matrices presented herein. Typically, chromium will be present in the edible formulation such that one serving will provide the recommended daily amount for a human (e.g., between 10 and 100 mcg/serving), or even more.

In alternative aspects of the inventive subject matter, it is contemplated that the matrix need not be limited to an aqueous extract of brewer's yeast, but that numerous alternative matrices may also be suitable, including (typically aqueous) extracts from various unprocessed and/or processed edible foodstuff. For example, fruit and/or vegetables may be pressed or otherwise disintegrated, optionally clarified (e.g., via filtration) to provide a liquid matrix that can be further processed (e.g., concentration, physical or chemical separation, etc). prior to addition of the chromium. Where desirable, multiple and different matrices may be combined (e.g., yeast matrix and fruit matrix, or water soluble extracts of one or more edible plant portions with filtered yeast disintegrate). Similarly, suitable matrices may also be produced from animal material.

Additionally, contemplated metal-fortified matrices may also be prepared from a complex matrix that is combined with one or more known and defined ligands for chromium or another metal, including nicotinic acid, polynicotinic acid, picolinate, various amino acids (proteinogenic and/or non-proteinogenic), carnosine, carnitine, citrate, etc. Thus, it should be appreciated that mixed complexes between a component of the matrix, a known ligand, and the metal are also deemed suitable.

Depending on the specific composition and/or further processing, it is generally preferred that the matrix is water soluble to a significant degree (i.e., at least 50 wt %, and more typically at least 70 wt %), and it is particularly preferred that the chromium-fortified matrix is substantially completely water soluble. To that end, processing steps in the preparation of the matrix may be included to remove water insoluble material, and particularly preferred processing steps include physical separation (e.g., sedimentation, centrifugation, filtration, etc.), chemical separation (e.g., phase separation with hydrophobic solvent, adsorption on hydrophobic matrix, etc.), and all reasonable combinations thereof. Such processing steps may be performed before, concurrent with, or after addition of the chromium. It should be noted that chromium picolinate, chromium niacin and heretofore known chromium yeast are all water insoluble. Consequently, it can be expected that the bioavailability is accordingly diminished. In contrast, all or almost all of the compounds contemplated herein are substantially completely water soluble, sufficiently stable, and bioavailable to a relatively large degree.

It should still further be recognized that numerous metals other than chromium are also contemplated, and all metals and metal ions suitable for human and mammalian ingestion are deemed appropriate. For example, alternative metals include ionic forms of Na, Mg, Ca, Zn, I, Co, Cu, V, Fe, Ni, and all reasonable combinations thereof etc. Most preferably, metal-fortified matrices are at least partially dehydrated (typically freeze-dried, evaporated, etc), and may then be packaged into a bulk preparation, individual dosage forms, or incorporated into another edible product. In still further contemplated aspects, numerous non-metal elements (e.g., group 13-16 elements) are also contemplated, and especially include those of nutritional significance. For example, suitable non-metal elements include B, Si, and Ge. Regardless of their chemical nature, it is generally preferred (but not necessary) that the element that is bound to the matrix is in ionic form. Furthermore, it should be noted that the absorption maximum of alternative metal or non-metal complex matrices will vary, and the exact position of the maximum will predominantly depend on the ligand and the synthetic protocol. Nevertheless, it is contemplated that the optimum biological activity will be correlated with spectral characteristics, and particularly with an absorbance maximum in the UV and/or VIS range.

Based on various experiments (see below) and further observations (data not shown), the inventors discovered that the biological activity of known and contemplated $Cr-3^+$ complexes is correlated with their spectral characteristics. More specifically, the position of an absorption maximum in the range of between 500 nm and 600 nm correlated with the vigor of the biological response. While not limiting to the inventive subject matter, the inventors contemplate that the chemical stability of the chromium complexes with different ligands is directly associated with the position of a maximum in the visible spectrum, wherein the most suitable stability (i.e., stability that provides highest bioavailability) of a chromium complex is that of a complex having an absorption maximum at about 560 nm.

Viewed from a different perspective, the stability of a chromium complex is a predictor for its biological activity. Thus, if complexes are too stable (e.g., Cr-picolinate) biological activity is low, and the same is true if the complexes are very unstable. For example, relatively stable complexes appear to be comparably bioavailable, but once they reach the target cells they do not readily transfer the chromium atom to a Cr-specific binding protein(s). On the other hand, relatively week complexes are typically unstable and are therefore not sufficiently bioavailable as insoluble chromium hydroxide is formed in the digestive tract upon dissociation of the chromium ion from the complex. Therefore, only chromium complexes of an intermediate stability are both bioavailable and active in target cells since they transfer their Cr-ion faster and easier than strong complexes would do. Consequently, the inventors contemplate chromium complexes, and especially water soluble complex chromium-containing matrices that have an absorption maximum at between 530 nm to 580 nm, more preferably between 545 nm to 575 nm, and most preferably between 550 nm to 570 nm.

It should be noted that the association between the wavelength of absorption in the range between 500 nm and 600 nm and the biological activity may be used to select for, design, and/or modify one or more ligands for a chromium-3+ ion. Similarly, selected products may be advertised as having an increased biological activity (e.g., reduce fasting blood glucose, improve glucose tolerance, reduce LDL cholesterol, etc.) based on the confirmed position of an absorption maximum (e.g., between 530 nm to 580 nm, more preferably between 545 nm to 575 nm, and most preferably between 550 nm to 570 nm).

In still further contemplated aspects, compositions according to the inventive subject matter may be further combined with a variety of other nutritional components, wherein such combinations exhibit additive, or even synergistic, effect with respect to their intended effect. Especially preferred combinations of chromium-containing water-soluble matrices include those in which the combinations are intended to positively affect the metabolism of a person. For example, it is known that chromium positively influences glucose utilization. Therefore, all known nutritional supplements for improving glucose utilization are especially contemplated herein. Similarly, chromium is also known to improve insulin sensitivity. Therefore, all known nutritional supplements for treatment or prevention of diabetes are especially contemplated suitable for use herein. Furthermore, chromium has also been implicated in prevention and/or improvement of elevated cholesterol. Consequently, all known nutritional supplements for treatment or prevention of heart disease or elevated cholesterol are especially contemplated appropriate. Still further, it is known in the art that chromium may also have an anabolic effect. Therefore, all known dietary supplements for increase of muscle mass are considered suitable for combination with contemplated chromium-containing matrices. Further particularly preferred combinations include those in which chromium-containing matrices are combined with metabolic enhancers, and especially conjugated linoleic acid and/or conjugated linoleic alcohol. Yet other preferred combinations include those in which an anabolic agent (e.g., DHEA) is combined with contemplated chromium-containing matrices.

EXAMPLES

The following abbreviations are used: CROA-1C (Chromium-Citrate-Aminooxyacetate); CROA-1 (Chromium-mono-Aminooxyacetate)—1 mmol sodium bicarbonate; CROA-2 (Chromium-bis-Aminooxyacetate)—2 mmol sodium bicarbonate; CROA-3 (Chromium-tris-Aminooxyacetate)—3 mmol sodium bicarbonate; CROX-1C (Chromium-Citrate-Oxamate); CROX-1 (Chromium-mono-oxamate) 1 mmol sodium bicarbonate; CROX-2 (Chromium-bis-oxamate) 2 mmol sodium bicarbonate; CROX-3 (Chromium-tris-oxamate) 3 mmol sodium bicarbonate; CROC-1 (Chromium-mono-Citrate); CROC-2 (Chromium-di-Citrate); HEX (ChromEx) (Chromium-chloride in YEX); YEX yeast extract;

Defined Ligands for Chromium-3+ Ions

Particularly striking examples include certain reference complexes (chromium complexes with oligopeptides [sequence data not shown]), which were labeled CPC5 (chromium-penta-oligopeptide), CPC3R (chromium-tri-oligopeptide-red), and CPC3V (chromium tri-oligopeptide-violet). Each of these reference complexes were prepared by reacting one mole of $Cr^{3+}$ with five or three moles of the same oligopeptide under different experimental conditions. Depending on the reaction conditions (typically reaction time and temperature, as well as slightly acidic, neutral, or slightly alkaline medium), products were obtained with distinct spectral characteristics. Thus, it is especially noted that the reaction conditions (here: control of temperature and pH) may significantly affect the spectral properties of an otherwise chemically identical composition.

For example, CPC3 compounds are prepared by dissolving CC-hh in 3 ml water; the oligopeptide is dissolved in 3 ml water and quickly mixed with the CC-hh solution. A precipitate forms; the product is heated for a short time and 252 mg SB are slowly added. Heat 2 hours at boiling water bath. The final pH of this preparation is basic. In contrast, CPC3R is prepared by dissolving CC-hh in 6 ml water. Heat at the boiling water bath for a short time. Add slowly to hot solution solid oligopeptide. No precipitate forms. Heat for another 10 minutes and then add slowly and cautiously 160 mg SB. No precipitate forms. On prolonged heating (two to three hours) the solution stays clear. The final color is in between red and violet, closer to red. The final pH is close to neutral. In further contrast, CPC3V is produced by dissolving CC-hh in water (6 ml). Heat and add slowly oligopeptide. No precipitate forms, and no SB is added. Heat for 2 hours at a boiling water bath. The product solution stays clear and has a distinct violet color. The final pH is acidic.

Exemplary synthesis of other defined complexes: 1 mmol (266 mg) of $CrCl_3$ hexahydrate (CC-hh) in all cases, and optionally 1 mmol (210 mg) of citric acid mono-hydrate (CA-mh) where indicated are combined with 1 mmol of ligand. The so prepared mixture is heated and sodium bicarbonate (for amounts see above) is carefully added. Heating is continued (typically in boiling water) bath for another 2 hours, and the resultant solution is then diluted or dehydrated as desired.

Yeast Matrix as Ligand for Chromium-3+ Ions

A solution of 400 mg water soluble yeast extract (Commercially available under the trade name AMBEREX) in 10 mL water is prepared and filtered if needed. 266 mg CC-hh are added and the resultant solution is kept for 2 hours at room temperature. If desired, the so prepared chromium-fortified matrix is filtered and dehydrated. It contemplated that similar to the CPC protocol given above, (a) a change in the pH of the resultant solution and/or (b) moderate temperature modifications will provide modified products in which the position of the absorbance maximum will vary. For example, it is contemplated that acidification of the yeast extract may provide a hypochromatic shift of the absorbance maximum ("ChromexA" in FIG. 1), while alkalinization may provide a hyperchromatic shift ("ChromexB" in FIG. 1). FIG. 1 depicts a graph in which the position of the absorbance maximum of various compounds is correlated with the biological activity (reduction of blood glucose increase, see below) of the compounds.

Test Results

In in vitro experiments (on total glucose uptake into L6 muscle cells at 100 nmol concentration), CPC5 increases on average 3.57, CPC-3R 4.00 and CPC-3V 4.45 fold over control. In vivo experiments gave much more dramatic differences, which are summarized in Table 1 below in which the increase in fasting blood glucose was measured after four weeks as compared to untreated animals:

TABLE 1

| DIABETIC RATS TREATED WITH | LAMDA MAX. | BLOOD GLUCOSE INCREASE |
|---|---|---|
| Cr-picolinate | 504 nm | 2.37 (95.56%) |
| Chromex | 569 nm | 1.88 (75.80% |
| CPC 5 | 531.5 nm | 2.15 (86.70%) |
| CPC3R | 540.5 nm | 1.74 (70.16%) |
| CPC3V | 558 nm | 1.09 (43.95%) |
| Untreated | | 2.48 (100%) |

Based on the data from Table 1, it can be seen that there is a clear relationship between the position of the absorption maximum (lambda max) of the chromium complex (i.e., between the strength of the Cr-Ligand Coordination Bond) and its biological activity. The optimal range for an absorption maximum is around 560 nm.

In Vitro Glucose Uptake in L6 Muscle Cells Induced by Various Chromium Compounds Total glucose uptake was measure using fluorescent analog of glucose, 2-NBDG (2-(N-(7-nitrobenz-2-oxa-1,3-diazol-4-yl)amino)-2-deoxyglucose) from Molecular Probes Inc. L6 myoblastic cells were treated for 2 hrs with tested compounds in culture medium SkBM from Clonetics. After washing, cells were transferred to HBSA (Hepes-buffered Saline), pH 7.0 with 50 mcM of 2-NBDG without glucose. One minute later, cells were washed with ice-cold PBS, and fixed in −20 C 70% ethanol. Fluorescence was measured at 480/530 (excitation/emission). Table 2 below lists exemplary results.

TABLE 2

| Compounds | Conc. nM | Fold over Control | Range | Average |
|---|---|---|---|---|
| CrCl3 | 10 | 1.44, 1.23, 0.95, 3.38, 0.94, 1.50, 1.44, 2.1, 1.3, 1.34, 1.46 | 0.94-3.38 | 1.55 |
| | 100 | 1.46, 1.33, 4.05, 2.0, 2.44, 1.56, 2.30, 1.52, 1.93 | 1.33-4.05 | 2.05 |
| | 1000 | 1.64, 1.24, 3.05, 2.83, 2.76. 1.68, 1.60, 1.63, 2.42 | 1.24-3.05 | 2.08 |
| Chromex | 10 | 4.44, 1.66, 3, 1.70, 2.40, 1.50, 1.40, 1.51 | 1.40-4.44 | 2.15 |
| | 100 | 4.88, 3.94, 2.75, 2.01, 4.50, 2.40, 1.84, 2.29 | 1.84-4.88 | 3.07 |
| | 1000 | 3.83, 4.26, 4.10, 2.44, 3.90, 3.3 2.39, 1.94 | 1.94-4.26 | 3.26 |
| CPC3R | 10 | 3.5, 3.0, 2.5, 1.6 | 1.6-3.5 | 2.65 |
| | 100 | 4.5, 4.0, 4.5, 3.0, | 3.0-4.5 | 4.00 |
| | 1000 | 6.0, 2.60, 3.20, 2.0, | 2.0-6.0 | 3.45 |
| CPC3V | 10 | 4.70, 1.88, 2.0, 3.0, 1.71 | 1.71-4.70 | 2.65 |
| | 100 | 8.50, 2.20, 4.9, 2.2, | 2.20-8.50 | 4.45 |
| | 1000 | 4.10, 2.90, 3.00, 3.40, 2.10 | 2.10-4.10 | 3.10 |
| CPC5 | 10 | 2.50, 1.77, 1.60, 1.30 | 1.30-2.50 | 1.73 |
| | 100 | 3.17, 6.10, 3.2, 2.10, | 2.10-6.10 | 3.57 |
| | 1000 | 3.20, 4.50, 2.60, 2.60 | 2.60-4.50 | 3.22 |
| CROA-1 | 10 | 1.41, 1.66, 2.10, | 1.41-2.10 | 1.72 |
| | 100 | 2.12, 2.16, 2.80, | 2.12-2.80 | 2.36 |
| | 1000 | 2.58, 2.10, 2.50 | 2.10-2.58 | 2.39 |
| CROA-1C | 10 | 1.08, 1.07, 1.44, | 1.07-1.44 | 1.19 |
| | 100 | 1.32, 1.35, 1.90 | 1.32-1.90 | 1.52 |
| | 1000 | 1.48, 1.96, 2.06 | 1.48-2.06 | 1.83 |

In Vivo Activity of Selected Chromium Compounds

Streptozocin-induced insulin deficient rats were used to evaluate the insulin potentiating activity of several compounds. Steptozocin causes damage of pancreas resulting in drastically reduced secretion of insulin. As consequence, these rats develop severe hyperglycemia. So far, certain known chromium compounds were known to potentiate action of insulin, however, the actual mechanism was not clearly understood. Only recently, chromium was found to stimulate AKT (protein kinase B), thus possibly inducing glucose uptake to muscle cells also in a insulin-independent way. In our studies in vivo, chromium compounds were provided in drinking water for four weeks at a concentration of about 42 µg/kg. Vein blood was collected following four hrs fasting and used for fasted blood glucose level test. The study results for two tests are given below in Table 3 in which the increase in blood glucose in given as a fold increase over four weeks.

TABLE 3

| Compound | Fasted Blood Glucose |
|---|---|
| STUDY 1 | |
| Untreated | 1.95 |
| CrCl3 | 1.32 |
| CPC3V | 0.80 |
| CPC5 | 1.02 |
| CrPic | 2.02 |
| Chromex | 1.55 |
| CrNiacin | 1.91 |
| Metformin | 0.96 |
| STUDY 2 | |
| Untreated | 2.48 |
| CrPic | 2.37 |
| Chromex | 1.88 |
| CPC3R | 1.74 |
| CPC3V | 1.09 |
| CPC5 | 2.15 |

These results show quite dramatic improvement of glucose transport in insulin-deficient rats. These rats are hypoinsulinemic and hyperglycemic due to severe pancreatitis conditions. Improvement under such conditions indicate that the treatment overpass insulin-deficiency and stimulate glucose utilization.

Thus, specific embodiments and applications of compositions and methods for improved chromium complexes have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. Method of manufacturing a nutritionally acceptable composition for mammalian consumption, comprising: combining a water soluble fraction of a cellular lysate with a chromium-3$^+$ salt; reacting the water soluble fraction of the cellular lysate with the chromium-3.sup.+ salt to form a substantially completely water soluble chromium-3$^+$ containing complex matrix; obtaining data that establish that potency of reduction of fasting blood glucose in vivo is dependent on an absorption maximum of the chromium-3$^+$-containing complex matrix in aqueous medium, wherein the absorption maximum is at a wavelength between 530 nm and 580 nm; adjusting the pH in the reacting step such that the absorption maximum of the substantially completely water soluble chromium-3$^+$-containing complex matrix is at the wavelength between 530 nm and 580 nm, and including the chromium-3$^+$-containing complex matrix into the composition in an amount effective to reduce blood glucose in a mammal in need thereof when the composition is orally administered to the mammal.

2. The method of claim 1 wherein the cellular lysate is a brewer's yeast extract or a dehydrated cellular extract.

3. The method of claim 1 wherein the absorption maximum is at a wavelength between 550 nm and 570 nm.

4. The method of claim 1 further comprising a step of including into the composition a metal in ionic form selected from the group consisting of Na, Mg, Ca, Zn, I, Co, Cu, V, Fe, and Ni.

5. The method of claim 1 wherein the composition is formulated as a beverage, a bar, a cereal, or a pill.

6. The method of claim 1 wherein the chromium-3.sup.+ is present in the composition in an amount effective to provide 10 to 100 mcg chromium-3.sup.+ per dosage unit.

7. The method of claim 1 wherein the composition is further effective to reduce cholesterol.

8. The method of claim 1 wherein the composition is further effective to increase at least one of glucose utilization, insulin sensitivity, and muscle mass.

9. The method of claim 1 further comprising a step of including into the composition at least one of an anabolic agent, a conjugated linoleic acid, and a conjugated linoleic alcohol.

10. The method of claim 1 wherein the composition is formulated as a multivitamin supplement, an edible formulation, or a drink.

* * * * *